(12) United States Patent
Kindler et al.

(10) Patent No.: US 6,337,429 B1
(45) Date of Patent: Jan. 8, 2002

(54) METHOD FOR SEPARATING A $C_4$-HYDROCARBON MIXTURE

(75) Inventors: Klaus Kindler, Harthausen; Hubert Puhl, Ludwigshafen, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/673,634
(22) PCT Filed: Apr. 13, 1999
(86) PCT No.: PCT/EP99/02470
  § 371 Date: Oct. 27, 2000
  § 102(e) Date: Oct. 27, 2000
(87) PCT Pub. No.: WO99/55647
  PCT Pub. Date: Nov. 4, 1999

(30) Foreign Application Priority Data

Apr. 27, 1998 (DE) .......................... 198 18 810

(51) Int. Cl.⁷ .............................. C07C 7/00; C07C 7/10; C10G 21/04; C10G 21/00; C10G 21/20
(52) U.S. Cl. ..................... 585/864; 585/860; 585/833; 208/317; 208/313; 208/320; 208/326; 208/330; 208/333
(58) Field of Search ............... 208/317, 313, 208/320, 326, 330, 333; 585/860, 864, 833

(56) References Cited

U.S. PATENT DOCUMENTS

| | | | | |
|---|---|---|---|---|
| 3,001,608 A | | 9/1961 | Lorenz et al. | |
| 4,166,771 A | * | 9/1979 | Haskell et al. | 203/58 |
| 4,277,314 A | | 7/1981 | Lindner et al. | |
| 4,292,141 A | | 9/1981 | Lindner et al. | |
| 4,555,312 A | * | 11/1985 | Ogura | 203/29 |
| 5,242,550 A | * | 9/1993 | Asselineau et al. | 203/58 |
| 6,040,489 A | * | 3/2000 | Imai | 585/260 |

FOREIGN PATENT DOCUMENTS

| | | |
|---|---|---|
| DE | 10 59 436 | 6/1959 |
| EP | 0 005 788 | 12/1979 |
| EP | 0 009 630 | 4/1980 |
| EP | 0 141 356 | 5/1985 |

OTHER PUBLICATIONS

V. A. Gorshkov, et al., The Soviet Chemical Industry, No. 11, pp. 719–723, "Comparison Of Processes Of Separating And Purifying Butadiene –1, 3," Nov. 1971.

* cited by examiner

Primary Examiner—Marian C. Knode
Assistant Examiner—Tam M. Nguyen
(74) Attorney, Agent, or Firm—Oblon, Spivak, McClelland, Maier & Neustadt, P.C.

(57) ABSTRACT

A $C_4$-hydrocarbon mixture essentially containing 1,3-butadiene, butenes, butanes and other $C_4$-hydrocarbons is separated into at least 4 fractions,
  a) the fraction (a) essentially comprising 1,3-butadiene,
  b) the fraction (b) essentially comprising butenes,
  c) the fraction (c) essentially comprising butanes and
  d) one or more fractions (d) essentially comprising 1,3-butadiene and the other $C_4$-hydrocarbons,
by extractive distillation by means of N-methyl-2-pyrrolidinone or an aqueous solution of N-methyl-2-pyrrolidinone (NMP).

9 Claims, 5 Drawing Sheets

METHOD FOR SEPARATING A C$_4$-HYDROCARBON MIXTURE

Figure 1:
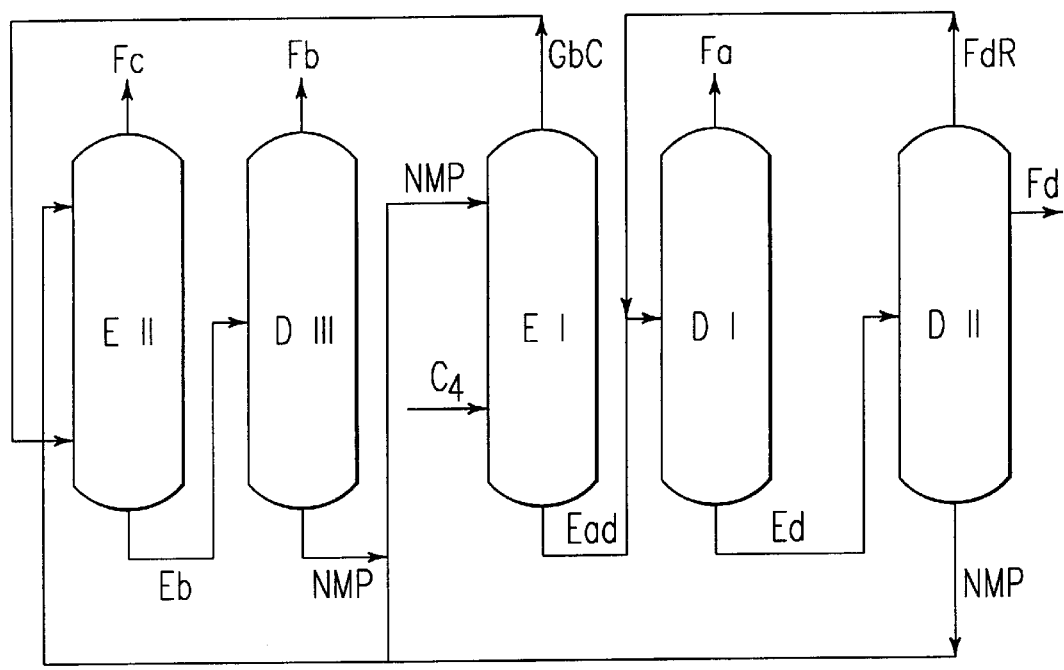

The present invention relates to a process for separating a C$_4$-hydrocarbon mixture essentially containing 1,3-butadiene, butenes, butanes and other C$_4$-hydrocarbons into at least 4 fractions,
  a) the fraction (a) essentially comprising 1,3-butadiene,
  b) the fraction (b) essentially comprising butenes,
  c) the fraction (c) essentially comprising butanes and
  d) one or more fractions (d) essentially comprising [lacuna] the other C$_4$-hydrocarbons,
  by extractive distillation by means of N-methyl-2-pyrrolidinone or an aqueous solution of N-methyl-2-pyrrolidinone (NMP),
  wherein
  1. the gaseous C$_4$-hydrocarbon mixture is first brought into contact with NMP in an extraction zone (I), the 1,3-butadiene and the other C4-hydrocarbons being essentially completely absorbed by the NMP but the butenes and butanes remaining essentially in the gas phase;
  2. the unabsorbed butenes and butanes (gas stream bc) and the extraction solution formed in step 1 (extraction solution ad) are removed from the extraction zone (I);
  3. the extraction solution (ad) is transferred to a desorption zone (I) at a lower pressure and/or higher temperature than the extraction zone (I) and 1,3-butadiene is desorbed from the extraction solution (ad), the main part of the other C$_4$-hydrocarbons remaining in the liquid phase;
  4. the extraction solution formed in stage 3 (extraction solution d) and the desorbed 1,3-butadiene (fraction a) are removed separately from the desorption zone (I) and, if required, a part of the fraction (a) is returned to the extraction zone I;
  5. the extraction solution (d) is transferred to a second desorption zone (II) at a lower pressure and/or higher temperature than the desorption zone (I) and having a pressure and/or temperature gradient, and the other C$_4$-hydrocarbons and the 1,3-butadiene still remaining therein are fractionally desorbed from the extraction solution (d) as at least two separate fractions (d), with the content of the other C$_4$-hydrocarbons being at least 10 times higher in at least one of the fractions (fractions d) than in the extraction solution (d), based on the content of all C$_4$-hydrocarbons, and the content of the other C$_4$-hydrocarbons being correspondingly lower in at least one of the fractions (fractions dR) than in the fractions (d), based on the content of all C$_4$-hydrocarbons,
  6. the NMP, formed in the desorption zone (II) and essentially free of C$_4$-hydrocarbons, and the fractions (d) and (dR) are removed separately from the desorption zone II, and one or more fractions (dR) are returned to the desorption zone (I),
  7. the gas stream (bc) is first brought into contact with the NMP formed in step 6 in an extraction zone (II), the butenes being essentially completely absorbed by the NMP but the butanes remaining essentially in the gas phase;
  8. the unabsorbed butanes (fraction c) and the extraction solution formed in step 1 (extraction solution b) are removed from the extraction zone (II);
  9. the extraction solution (b) is transferred to a desorption zone (III) at a lower pressure and/or higher temperature than the extraction zone (II) and the butenes are desorbed from the extraction solution (b);
  10. the NMP, formed in step 9 and essentially free of C$_4$-hydrocarbons, and the desorbed butenes (fraction b) are removed from the desorption zone (III);
  11. the NMP formed in step 9 is recycled to one of the extraction zones.

This process is shown schematically in FIG. 1.

A process for separating 1,3-butadiene from a C$_4$-hydrocarbon mixture is disclosed, for example, in DE-A-2724365. Briefly, a butane/butene mixed fraction, a 1,3-butadiene fraction and a fraction which contains the other C$_4$-hydrocarbons are obtained in this process from a C$_4$-hydrocarbon mixture which contains butanes, butenes, 1,3-butadiene and other C$_4$-hydrocarbons, by extractive distillation with NMP as absorbent over various absorption and desorption stages. In the entire process, the NMP required passes through a closed circulation. NMP which no longer contains any C$_4$-hydrocarbons (unladen NMP) is first laden with the C$_4$-hydrocarbon mixture at the beginning of a cycle, passes through the various absorption and desorption stages until, at the end of a cycle, unladen NMP is provided by completely desorbing the C$_4$-hydrocarbons. The process is distinguished by the fact that the individual stages are particularly advantageously coupled via indirect heat exchange processes.

The separation of 1,3-butadiene and 2-butenes into separate fractions and the separation of 1,3-butadiene and acetylenes into separate fractions from C$_4$-hydrocarbon mixtures have been described by V. A. Gorshkov et al. in the publication The Soviet Chemical Industry, No. 11, November 1971.

EP-A-141356 likewise relates to the separation of a 1,3-butadiene fraction from a C$_4$-hydrocarbon mixture by means of extractive distillation using NMP. The use of columns in which absorption and desorption zone are integrated in a single column in each case make this process particularly economical.

EP-A-5788 discloses a process for separating a 1,3-butadiene fraction and a butyne fraction from a C$_4$-hydrocarbon mixture by means of extractive distillation using NMP.

EP-A-9630 relates to a process for separately removing styrene and 1,3-butadiene from a mixture which otherwise contains C$_4$-hydrocarbons, the styrene first being separated from the mixture by distillation and 1,3-butadiene being separated from the remaining mixture by means of extractive distillation.

U.S. Pat. No. 5,242,550 discloses the separation of a butene/butane mixture by means of extractive distillation using NMP as absorbent.

It is an object of the present invention to provide a process which permits the separation of a C$_4$-hydrocarbon mixture into a butane fraction, butene fraction, 1,3-butadiene fraction and a fraction which contains the other C$_4$-hydrocarbons in a particularly efficient and economical manner. In particular, the required quantities of energy and the capital costs should be particularly low in this process.

We have found that this object is achieved by the process described at the outset.

The process can be applied to C$_4$-hydrocarbon mixtures which contain 1,3-butadiene, butenes, butanes and other C$_4$-hydrocarbons plus very small amounts of C$_3$- and C$_5$-hydrocarbon impurities.

Such C$_4$-hydrocarbon mixtures are obtained, for example, as C$_4$ fractions in the production of ethylene and/or propylene by thermal cleavage of a petroleum fraction, for example of liquefied petroleum gas (LPG), naphtha, gas oil or the like as hydrocarbon fraction. Furthermore, such $C_4$ fractions are obtained in the catalytic dehydrogenation of n-butane and/or n-butene. The $C_4$ fractions obtain [sic], as a rule, butanes, n-butene, isobutene, 1,2 butadiene, vinylacetylene, ethylacetylene and 1,2-butadiene [sic] and may contain small amounts of $C_5$-hydrocarbons, the 1,3-butadiene content being in general from 10 to 80, preferably from 20 to 70, in particular from 30 to 60, percent by weight while the content of vinylacetylenes, ethylacetylene and 1,2-butadiene (referred to below as other hydrocarbons) together in the $C_4$ fractions generally does not exceed 5 percent by weight.

The novel process can advantageously be employed in particular to those $C_4$-hydrocarbon mixtures which contain from 10 to 80% by weight of 1,3-butadiene;

from 10 to 60% by weight of butenes;

from 5 to 40% by weight of butanes;

from 0.1 to 5% by weight of other $C_4$-hydrocarbons and from 0 to at most 5% by weight of $C_3$- and $C_5$-hydrocarbons.

The n-methyl-2-pyrrolidinone or its aqueous solution employed as selective solvent (N-methyl-2-pyrrolidinone and its aqueous solution abbreviated to "NMP" for short hereinafter) is generally a conventional industrial product which may contain up to 15% by weight of water.

The extraction zones are preferably in the form of columns through which the gas streams are passed countercurrently to the NMP.

In step 1, the $C_4$-hydrocarbon mixture to be separated is first fed in gaseous form with NMP into an extraction zone (I) and brought into contact with one another there, the 1,3-butadiene and the other $C_4$-hydrocarbons being essentially completely absorbed by the NMP but the butenes and butanes remaining essentially in the gas phase. In the NMP and $C_4$-hydrocarbon mixture fed in, the ratio of NMP to $C_4$-hydrocarbon mixture is from 5:1 to 20:1 in the extraction zone (I).

The generally known extraction methods are suitable for this extraction step.

From the extraction zone (I), in general a gas stream which [lacuna] in particular unabsorbed butanes and butenes and, if $C_3$- and $C_5$-hydrocarbons are present as impurity in the $C_4$ mixture, also propane, propene and propadiene plus traces of $C_5$-hydrocarbons (gas stream bc) is removed at the top of column and the extraction solution (extraction solution ad) is removed from the bottom of the column.

The extraction solution (ad) contains in general only from 0 to 2% by weight of butenes and butanes, plus, if present, propyne and/or almost the total amount of $C_5$-hydrocarbons.

The gas stream (bc) contains, in addition to the butenes and butanes, in general only from 0 to 1% by weight of the 1,3-butadiene originally present in the $C_4$-hydrocarbon mixture and of the other $C_4$-hydrocarbons.

The extraction zone (I) is generally in the form of a scrubbing column with plates, dumped packings or structured packings as internals. These preferably have from 40 to 80 theoretical plates. The column pressure depends on the temperature of the cooling medium (well water, river water, sea water, refrigerants such as liquid propylene, liquid ammonia or brine). It is between 2 and 6 bar, preferably 4.5 bar. The temperature profile in the extraction zone is determined by the temperature of the NMP. It is advantageous to lower the temperature profile by partial condensation of the fraction (bc) because the separation efficiency is improved at lower temperature. A typical value for the condensation is 20%. This results in a temperature of from 40 to 60° C. at the top of the column.

For the desorption of the 1,3-butadiene from the extraction solution (ad), the latter is transferred to a desorption zone (I) at a lower pressure and/or higher temperature than the extraction zone (I) and 1,3-butadiene (1,3-butadiene fraction a) is desorbed from the extraction solution (ad), the main part of the other $C_4$-hydrocarbons, propyne and $C_5$-hydrocarbons remaining in the liquid phase.

Preferably, the pressure in the desorption zone (I) is the same as that in the extraction zone (I) and the temperature is from 20 to 25° C. higher than in the extraction zone (I).

The 1,3-butadiene fraction (a) removed from the desorption zone (I) usually has a purity of from 95 to 99% by weight.

The extraction solution (d) formed by desorption of 1,3-butadiene in the desorption zone (I) is then removed from the desorption zone (I) and transferred to a second desorption zone (II) at a lower pressure and/or higher temperature than the desorption zone (I). During transfer of the extraction solution (d) from desorption zone (I) to (II) it advantageously passes through a heat exchanger zone in which a part of the hydrocarbons in the extraction solution (d) evaporates, and this gas stream is directly fed back into the bottom of desorption zone (I). Pressure and temperature are chosen so that virtually all $C_4$-hydrocarbons still remaining in the NMP are desorbed; they are in general 1.5 bar and 150° C.

In desorption zone II there is fractional desorption from the extraction solution (d) of 1,3-butadiene still present therein and of the other $C_4$-hydrocarbons plus, where appropriate, [lacuna] and $C_5$-hydrocarbons still present therein as at least two separate fractions (d), with the content of other $C_4$-hydrocarbons being at least 10 times, in general from 10 to 100 times, preferably from 20 to 80 times, higher in at least one of the fractions (fraction d) than in the extraction solution (d), based on the content of all $C_4$-hydrocarbons, and the content of the other $C_4$-hydrocarbons being lower in at least one of the fractions (fractions dR) than in the fractions (d), based on the content of all $C_4$-hydrocarbons. The hydrocarbons in the extraction solution (d) are preferably fractionated in the desorption zone (II) into a fraction (d) and a fraction (dR), where fraction (d) preferably comprises essentially at least 20% by weight, particularly preferably from 20 to 40% by weight, of other $C_4$-hydrocarbons and otherwise butadiene, and fraction (dR) comprises essentially more than 80% by weight, particularly preferably from 85 to 95% by weight, of butadiene and otherwise other $C_4$-hydrocarbons.

The NMP formed in the desorption zone (II) and essentially free of $C_4$-hydrocarbons, and fractions (d) and (dR) are removed separately from the desorption zone II, and one or more of the fractions (dR) are returned to the desorption zone (I), e.g. to the bottom of the scrubbing column.

The pressure gradient in this case is preferably overcome by means of a compressor. The fraction (d) is normally treated countercurrently with water (condensate) in order to absorb most of the NMP present therein.

In general, the ratio by weight of the fractions returned to the desorption zone (I) to those removed from the system is from 20:1 to 80:1.

The desorption zone (II) consists in general of a main column with a side column. Both are designed as scrubbing columns. The main column generally contains packings because the low pressure drop thereof has particularly beneficial effects here. The main column should have from 10 to 15 theoretical plates. The side column generally has 10 practical plates. The pressure is generally from 1.5 to 1.6 bar; the temperature at the bottom of the main column is from 140 to 150° C. and at the top thereof is from 80 to 100° C. While the fractions (d) are removed as sidestream preferably at from 130 to 140° C., the fractions (dR) are normally taken off overhead.

If a 1,3-butadiene fraction having a particularly high purity is desired, the following procedure is preferably adopted:

The 1,3-butadiene fraction (a) which is removed from the desorption zone (I) is divided into two part streams of fraction (a1) and (a2), and fraction (a1) is returned to the extraction zone I (is preferably passed to the bottom of the extraction column I) and fraction (a2) is again brought into contact, in an extraction zone (III), with NMP which was recovered from the desorption zone (II) or (III), a part of the fraction (a2) and the predominant part of other $C_4$-hydrocarbons still contained as impurity in the fraction (a2) being absorbed by the NMP (extraction solution ax).

The unabsorbed part of the fraction (a2) (fraction a3) is removed separately from the extraction zone, and the extraction solution (ax) is returned to the extraction zone (I).

Figure 2:
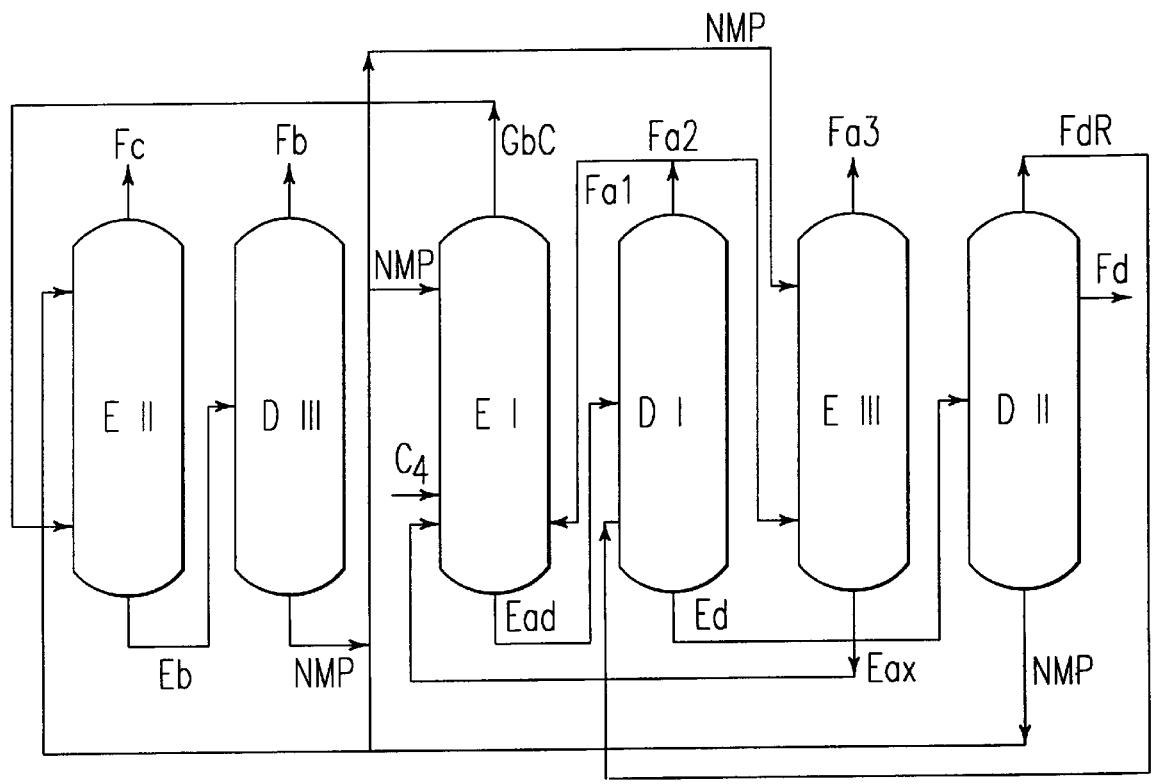

This variant is illustrated in FIG. 2.

The ratio by weight of NMP to 1,3-butadiene fraction (a) generally corresponds to from 1:3 to 1:7, depending on the composition of the initial $C_4$ mixture and the specifications for fraction (a3).

The ratio of the material streams of fractions (a1) and (a2) is normally from 1:1 to 4:1.

The 1,3-butadiene fraction (a3) still contains impurities in particular in the form of $C_3$- and $C_5$-hydrocarbons and 1,2-butadiene. These impurities are in general subsequently removed in two conventional distillation columns.

Regarding the design of the extraction column and the parameters of pressure and temperature, the same applies in general terms to the extraction zone (III) as to the extraction zone (I). The ratio of NMP fed in to the crude butadiene fraction (a2) corresponds to from 1:3 to 1:7.

The unabsorbed 1,3-butadiene and the 1,3-butadiene taken off from the extraction zone (III) normally has a purity of more than 98% by weight.

The gas stream (bc), optionally with the addition of the external added stream (gas stream Zbc is first brought into contact, in an extraction zone (II), with the NMP recovered in the desorption zone (II), the butenes being essentially completely absorbed by the NMP but the butanes remaining essentially in the gas phase.

The extraction zone (II) is in general in the form of a scrubbing column with plates, dumped packings or structured packings as internals. These must have from 30 to 70 theoretical plates in order to achieve a sufficiently good separation effect. The pressure in the extraction zone (II) is chosen so that the gas stream (bc) is able to pass from the extraction zone (I) without further technical assistance into the extraction zone (II). It also depends on the cooling medium available for condensing the fraction (c). A typical value for the pressure is 4.0 bar, provided water is used for cooling.

The scrubbing column is advantageously equipped in the top of the column with a back-wash zone which comprises, for example, 4 theoretical plates. This back-wash zone serves for recovering the NMP present in the gas phase by means of back-flow of liquid hydrocarbon, for which purpose fraction (c) has previously been condensed. It is possible at the same time to influence thereby the temperature profile in the extraction zone (III). It also applies in this case, as already mentioned in extraction zone (I), that a lower temperature promotes the separation efficiency. Typical temperatures at the top of the column are between 35 and 45° C.

The ratio by weight of NMP to gas stream (bc), including gas stream Zbc where appropriate, in the feed to extraction zone (II) is from 10:1 to 20:1, depending on the specifications for fractions (b) and (c) and the composition of the initial $C_4$ mixture and of the added stream Zbc.

In the extraction zone (II), a gaseous butane fraction (fraction c) and an extraction solution (b) containing the butene fraction (fraction b) are formed. If the extractive distillation is carried out as described above, a fraction (b) which is contaminated with up to 5% by weight of butanes and a fraction (c) which is contaminated with up to 15% by weight of butenes are obtained.

The extraction solution (b) is transferred to a desorption zone (III) at a lower pressure and/or higher temperature than the extraction zone (II), the butenes being desorbed from the extraction solution (b). The desorption of the butenes and of any other $C_4$-hydrocarbons contained therein as impurity can in principle be carried out similarly to the desorption of the other $C_4$-hydrocarbons in the desorption zone (II).

The desorption zone (III) may be, for example, in the form of a scrubbing column which has from 5 to 15, preferably from 8 to 10, theoretical plates and a back-wash zone with, for example, 4 theoretical plates. This back-wash zone serves for recovering the NMP present in the gas phase by means of a back-flow of liquid hydrocarbon, for which purpose the fraction (b) has previously been condensed. It is advantageous to provide packing beds as internals. The pressure at the top of the column is generally 1.5 and [sic] 1.6 bar. The temperature in the bottom of the column is generally from 130 to 150° C.

The NMP recovered in the desorption zone (III) is returned to the extraction zones (I), (II) and/or (III).

An additional advantage accrues when the NMP recovered in the desorption zone (III) is fed back only into the extraction zones (I) and (II), and the NMP recovered in the desorption zone (II) is essentially fed back into the extraction zone (III).

The advantage derives from the fact that the removal of butenes/butanes from a $C_4$-hydrocarbon mixture using NMP takes place more easily than the separation of a mixture of butenes and butanes into two high-purity butene and butane fractions. Moreover a single solvent circulation is maintained.

In contrast to the extraction zone (III), which requires high-purity degassed NMP, the quality of the NMP for the extraction zones (I) and (II) does not need to be so high. This signifies a gain economically in that the degree of degassing of the NMP, and thus the consumption of external steam for desorbing hydrocarbons in the desorption zone (III), does not need to be so high. In contrast to the NMP from the desorption zone (II), where from 0 to 10 ppm by weight of $C_4$-hydrocarbons are desired, it is perfectly possible for the NMP from the desorption zone (III) to have 1000 or more ppm by weight. This does not impair the purity of product fractions (b) and (c). On the other hand, however, a content of hydrocarbons reduces the boiling point of the solvent. Since the heat content of the NMP from the desorption zone (III) is utilized, however, for reasons of economy, it is not possible to continue reducing the boiling point by increasing the residual content of hydrocarbons indefinitely. The bottom temperatures of from 130 to 150° C. indicated previously result for these reasons. At a bottom temperature of 138° C., the resulting residual content of hydrocarbons is about 800 ppm by weight.

The novel process can be carried out particularly economically if the heat of the NMP which is obtained by boiling up the extraction solutions (b) and (d) is fed to the desorption zone (I), (II) and/or (III) by indirect heat exchange in a heat exchange zone, and the desorption is effected in these desorption zones by increasing the temperature in the desorption zone (I) relative to that in the extraction zone (I), and increasing the temperature in the desorption zone (II) relative to that in the desorption zone (I) and increasing the temperature in the desorption zone (III) relative to that in the extraction zone (II).

The separation of the fraction (a) (butadiene) from the $C_4$-hydrocarbon mixture is preferably carried out as described in DE-A-2724365. This part of the process is particularly preferably carried out as described in FIG. 3.

According to this process variant, the following procedure is adopted:

The extractive distillation is carried out in more than one column, in general in two columns which together have more than 100 practical trays. When using two columns, the absorption stage situated above the point at which the $C_4$-hydrocarbon mixture is fed into the extractive distillation zone is advantageously located in the first column and the concentration stage situated below the feed point of the hydrocarbon mixture is advantageously located in the second column, i.e. the feed point for the hydrocarbon mixture is at the top of the second column or preferably at the bottom of the first column. Preferably, no compression stage is located between absorption stage and concentration stage, and instead the pressure conditions maintained within the extractive distillation zone are those automatically established in the extractive distillation zone in the absence of compression and/or pressure reduction stages within the extractive distillation zone, so that the pressure at the bottom of the extractive distillation zone corresponds at least to the pressure at the top of the extractive distillation zone, in line with the usual pressure loss. As a rule, the pressure difference between top and bottom of the extractive distillation zone is from 0.1 to 3, preferably from 0.2 to 2, bar.

In general, pressures of from 1 to 9, preferably from 2 to 8, in particular from 3 to 7, bar are used in the extractive distillation zone. The pressures in the lower third of the extractive distillation zone, i.e. in the region which is occupied by the lower trays of the extractive distillation zone, which correspond to about a third of the total number of trays of the extractive distillation zone, are as a rule from 1.5 to 9, preferably from 2.5 to 8, in particular from 3.5 to 7, bar.

The extract taken off from the extractive distillation zones is first brought to a higher pressure than the pressure in the extraction distillation zone.

This can be effected, for example, by means of a liquid pump. In general, this pressure increase is effected essentially isothermally, i.e. the only temperature changes which occur, for example a temperature increase up to 1 °C., are those which are caused by the measure leading to the pressure increase, for example the pumping process. In general, the extract is brought to pressures which are from 1 to 20, preferably from 2 to 18, in particular from 3 to 15, bar above the pressure in the extractive distillation zone, in particular above the pressure in the lower third of the extractive distillation zone.

The extract under increased pressure is then heated in a heat exchange zone by indirect heat exchange with the selective solvent obtained as a bottom product from the solvent recovery zone. The selective solvent is recycled to the extractive distillation zone after the heat exchange. As a result of the heat exchange with the selective solvent, the temperature of the extract is generally increased by from 5 to 80° C., preferably 10 to 70° C., in particular from 15 to 60° C.

The heated extract is then let down by flash evaporation to a pressure which corresponds at least to the pressure in the extractive distillation zone, preferably at least to the pressure in the lower third of the extractive distillation zone, and is higher than the pressure in the downstream solvent recovery zone. It is critical for the pressure reduction that the vapor fraction of the extract, which fraction forms in the flash evaporation, can be returned to the extractive distillation zone without a compression stage. Accordingly, as a rule the pressure is let down in the flash evaporation to pressures which are from 0.05 to 2.0, preferably from 0.1 to 1, bar above the pressure at the feed point of the vapor fraction of the extract into the extractive distillation zone. The flash evaporation is carried out, for example, in an apparatus comprising a pressure reduction valve on an adiabatic evaporator, if required a phase separation vessel being provided downstream for better separation of the vapor and liquid phases forming in the flash evaporation.

The combination of heat exchange zone for the heat exchange between the extract from the extractive distillation zone and the selective solvent recycled from the solvent recovery zone with the downstream flash evaporation can be used in one stage. However, it is also possible to use more than one such combination, for example from 2 to 4, preferably 2 or 3, such combinations, advantageously connected in series. By using more than one of these heat exchange/flash evaporation stages and recycling the partstreams thus obtained to different feed points of the extractive distillation zone, the required separation efficiency of the extractive distillation and the dimensions of the extractive distillation column can be reduced. It is also possible to connect a further heat exchange zone between the last flash evaporation zone and the solvent recovery zone.

That vapor fraction of the extract which forms in the flash evaporation zone or zones and generally comprises from 20 to 80, preferably from 40 to 70, % by weight of the hydrocarbons in the extract is returned to the extractive distillation zone. In general, the returned vapor phase is passed into the lower third of the extractive distillation zone, preferably at the bottom of the extractive distillation zone, for example at a point which is located roughly at the height of the lowermost column tray. In the stepwise flash evaporation, vapor fractions contained in the individual stages can be returned, separately or after their combination, to the extractive distillation zone.

The liquid phase of the extract from the extractive distillation zone, which phase remains after flash evaporation, is fed to a solvent recovery zone which is operated at a lower pressure than the pressure in the flash evaporation zone. The remaining liquid extract phase is let down to the lower pressure in the solvent recovery zone, advantageously by means of an intermediate pressure reduction valve. In general, the pressure in the solvent recovery zone is from 0.1 to 8, preferably from 0.5 to 7, in particular from 1 to 6, bar lower than the pressure in the flash evaporation zone or zones. The solvent recovery zone may be operated, for example, as a gas expulsion zone or as a solvent stripper. In general, heat is supplied to the solvent recovery zone, for example via an indirect heat exchanger using steam (reboiler).

The NMP obtained as a bottom product of the solvent recovery zone and freed from the hydrocarbons is returned to the extraction stages (I) and (III) via the heat exchange zone in which the heat exchange with the extract from the extractive distillation zone takes place.

The product which is obtained from the solvent recovery zone contains the hydrocarbons and is in general taken off as a top stream or as a top and side stream, passes partly or if necessary completely initially through a compression stage and is fed to the extractive distillation zone after the compression. In the compression zone, the hydrocarbon stream is compressed to a pressure which corresponds at least to the pressure in the extractive distillation zone. In general, the hydrocarbon stream is compressed to pressures which are from 0.05 to 2, preferably from 0.1 to 1, bar above the pressure at the feed point of the vapor fraction of the extract into the extractive distillation zone.

Figure 3:
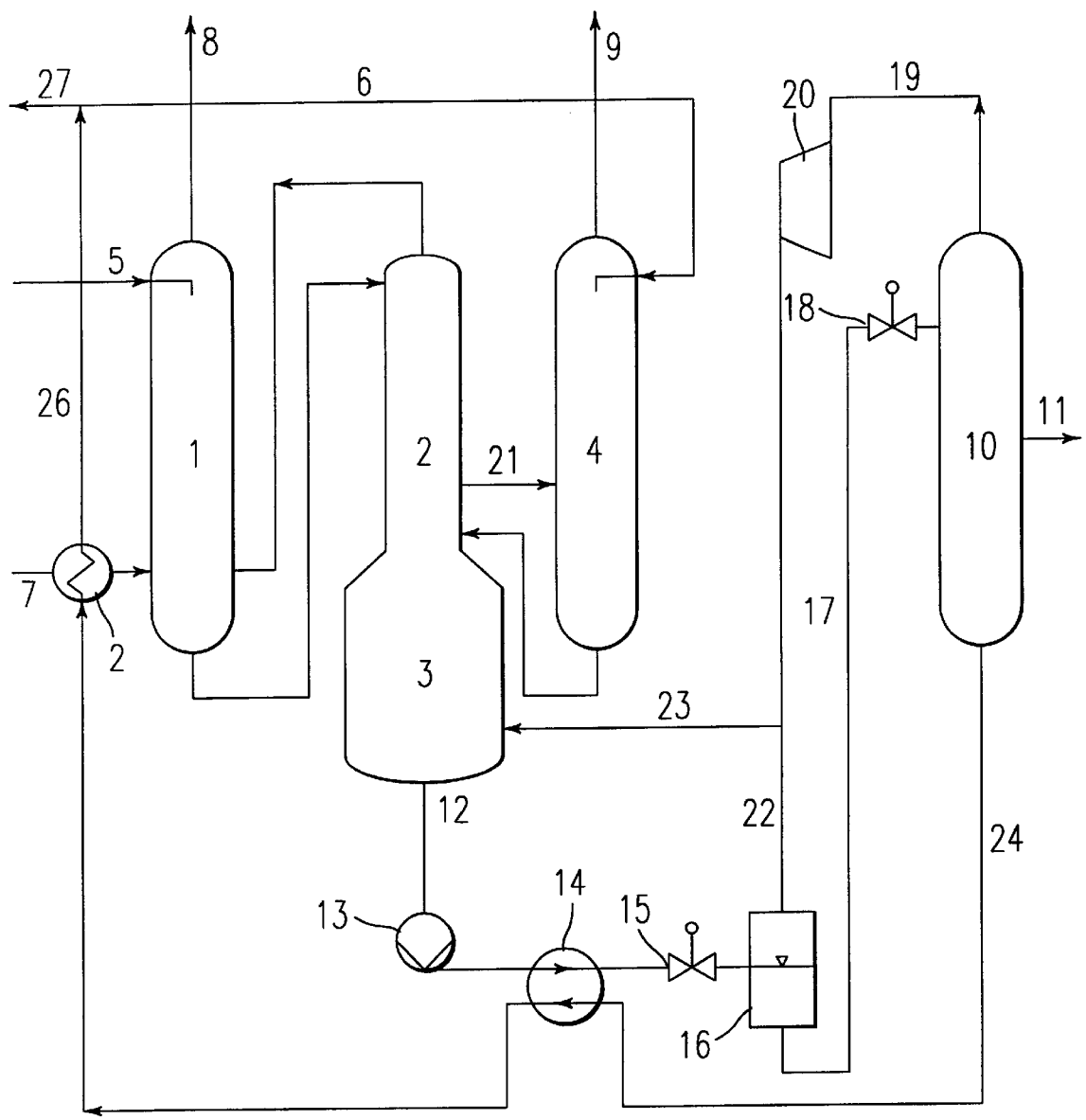

FIG. 3 is a schematic diagram of an embodiment of the preferred variant. In this embodiment, 2 extractive distillation zones are connected in series. The first extractive distillation zone is formed by column 1 and the upper tapered column section 2, while the second extractive distillation zone is formed by column 4 and the lower column section 3. The NMP is fed to the upper part of column 1 through line 5 and to the upper part of column 4 through line 6. A $C_4$-hydrocarbon mixture is fed to the bottom of column 1 via line 7.

The columns 2/3 and 4 are also directly connected. A gaseous part stream is removed from the column 2 and washed countercurrently with solvent through line 6.

At the top of the column 1, a refined product which consists essentially of butenes and butanes is taken off through line 8.

At the top of the column 4, an essentially pure 1,3-butadiene is taken off through line 9.

A gas stream containing essentially the other hydrocarbons and other impurities is removed via the side take-off of the column 10 through line 11.

The pressure in the column section 3 is about 5 bar. The extract taken off via line 12 is brought to 15 bar by a liquid pump 13 and then heated at from 70?C [sic] to 125?C [sic] in heat exchanger 14 by means of the NMP taken off from gas expulsion zone 10 via line 24 and essentially free of $C_4$-hydrocarbons. The heated extract is then passed through pressure reduction valve 15 and let down to a pressure slightly above 5 bar. While the gaseous phase formed in the phase separation tank 16 is immediately returned through line 22 and 23 to the column 3, the liquid phase, obtained after the flash evaporation, of the extract is fed through line 17 to another pressure reduction valve 18 where the pressure falls to the level of pressure in the column 10, normally 1.5 bar.

At the top of column 10, a hydrocarbon stream is taken off through line 19 and, after compression in the compressor 20, also fed through line 23 to the bottom of the column 3. It is important, for safety reasons, in this connection that the gas stream 19 is cooled by heat exchange (not depicted in FIG. 3) before entering the compressor 20 so that the temperature of the gas stream after emergence from the compressor does not exceed 110° C. The gas stream is normally cooled to 45° C.

The NMP which is virtually free of $C_4$-hydrocarbons and is taken off through line 24 and cooled in the heat exchanger 14 is fed through line 25 to the heat exchanger 2. It then passes through another heat exchanger (not depicted in FIG. 3) in which the temperature of the solvent is adjusted to 38° C. The amount of solvent arriving through line 26 is then divided into two part streams: line 6 leads to the column 4, while line 27 terminates in the additional extractive distillation zone (III) for separating butenes and butanes. The solvent returns from there through line 5.

In order to simplify the drawings, all the abovementioned back-wash zones with the flows of liquid hydrocarbons back to columns 1 and 4 have also been omitted. The abovementioned side column on the main column 10 is also absent from FIG. 3.

EXAMPLE

Figure 4:
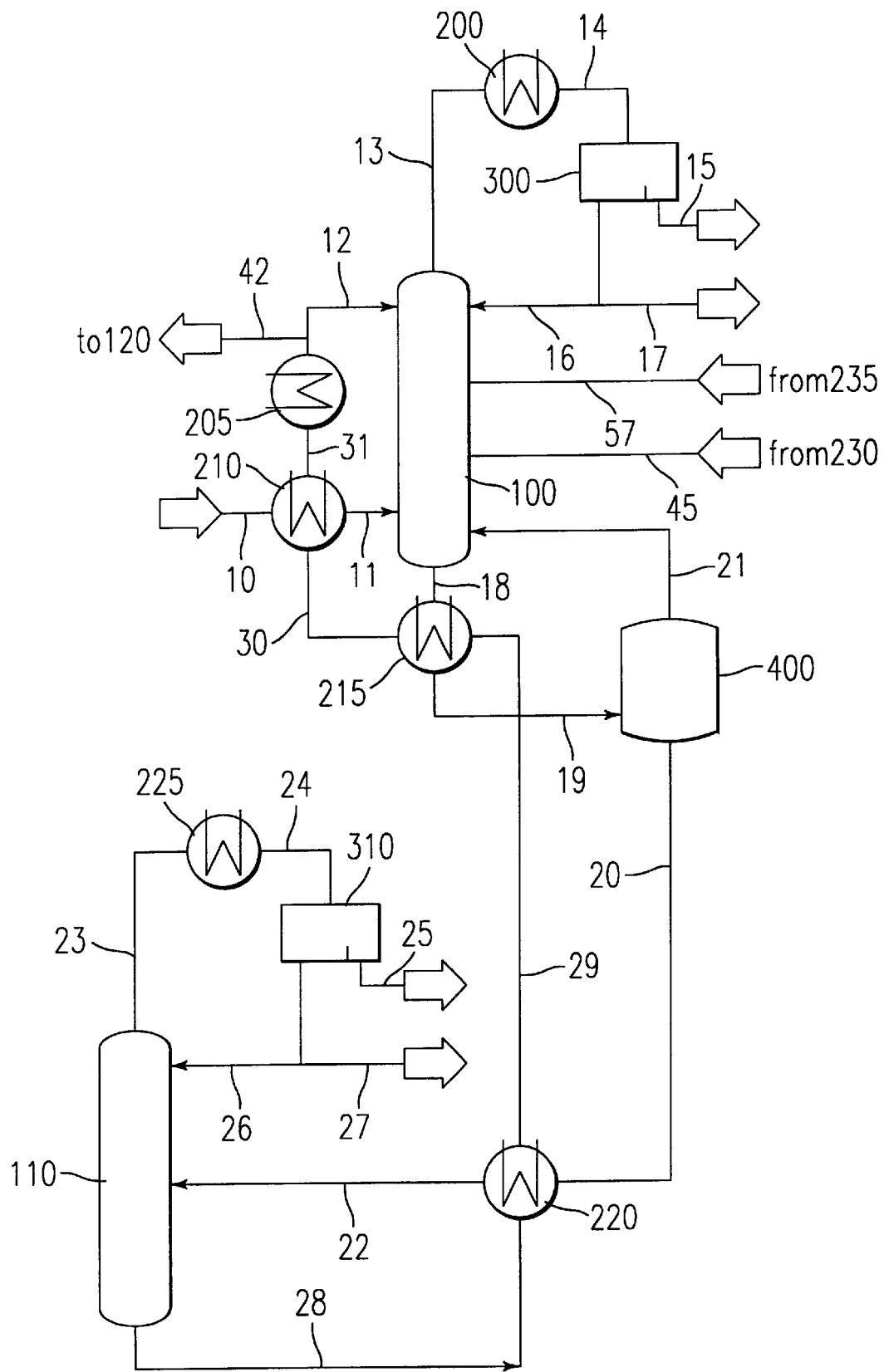
Figure 4A:
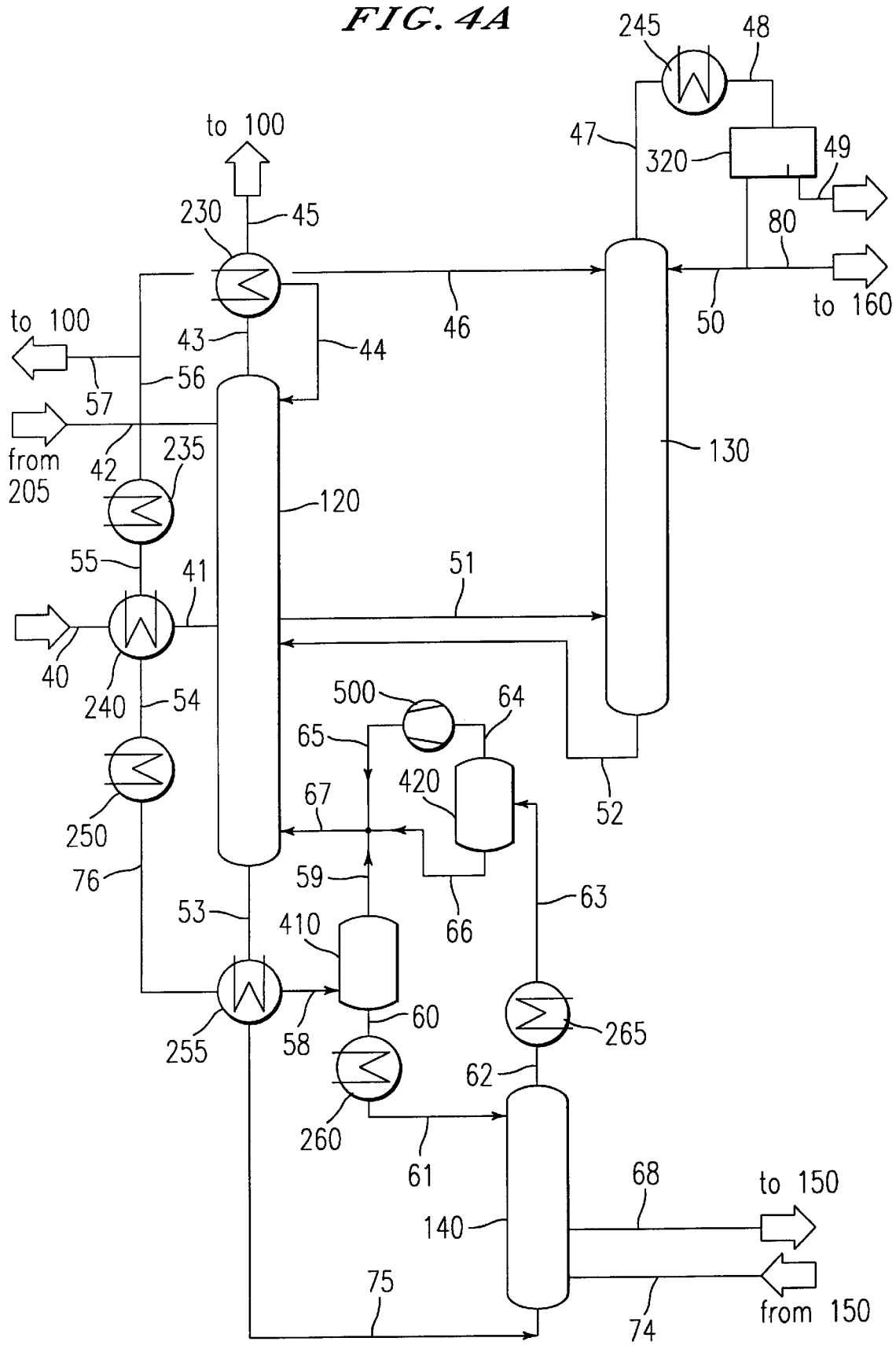
Figure 4B:
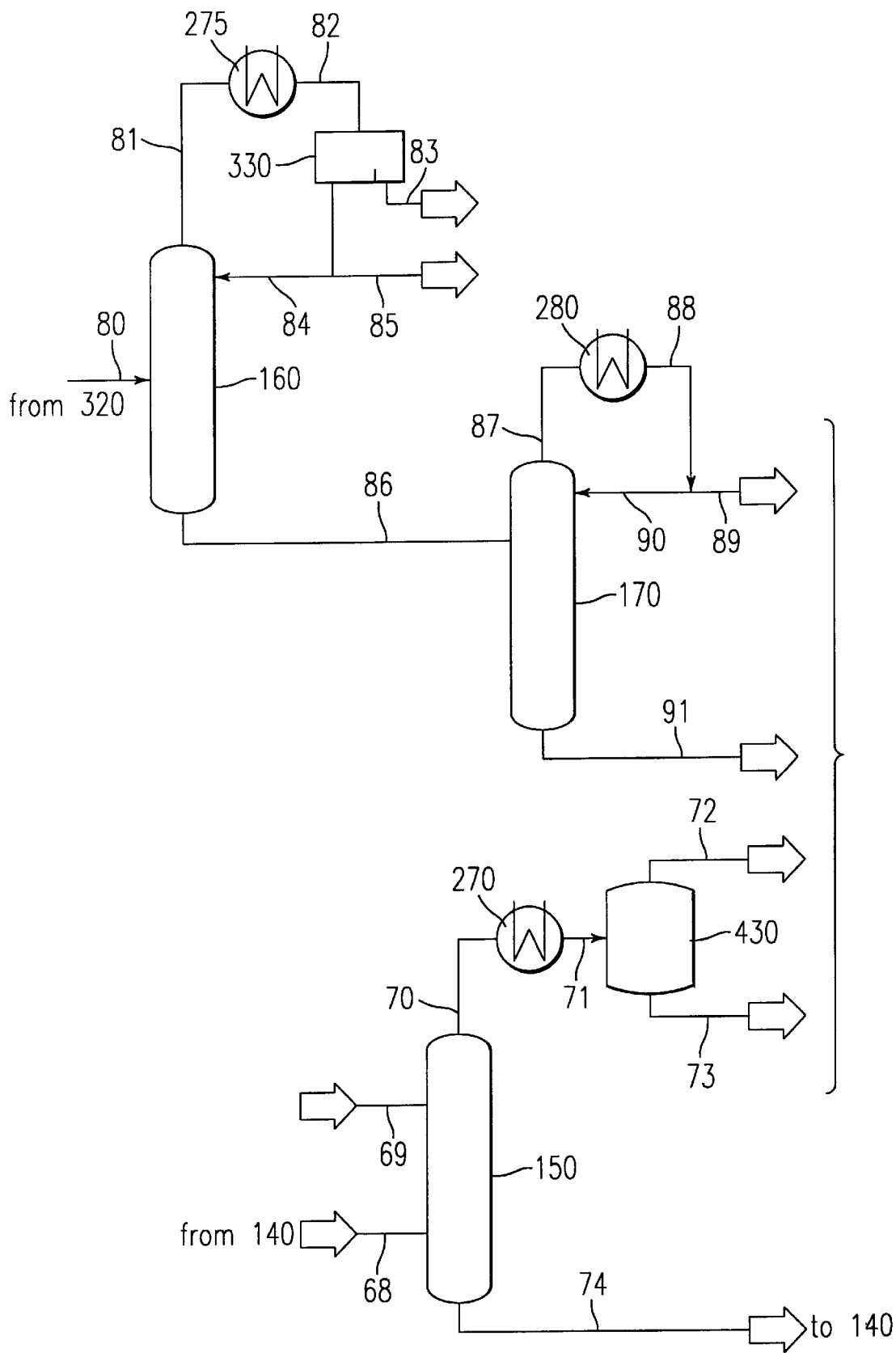

Compared with FIG. 3, the diagram of the process in the example is considerably more extensive (FIG. 4), even though all the pumps have been omitted from the figure in this case too. On the other hand, all the heat exchangers are detailed besides the columns because they are crucially involved in the economics of the process. Likewise, all the phase separators have been included in the diagram. The number assignment system is likewise evident from FIG. 4.

The extraction zone (I) and the desorption zone (I) are concealed behind column 120. Extraction zone (III) is column 130. The desorption zone (II) is represented by the two columns 140 and 150. Extraction zone (II) is the column 100 and desorption zone (III) is column 110. In addition, the two final distillation columns 160 and 170, in which the crude butadiene is finally brought up to specification, have been included, because they belong to the overall process.

The process has 3 incoming streams:
Stream 10: Added stream Zbc, containing butenes and butanes
Stream 40: $C_4$ feed
Stream 69: Condensate addition to reduce the NMP loss Composition [% by weight] and quantity [kg/h] of stream 10:

| | |
|---|---|
| n-Butane | 26.0 |
| i-Butane | 9.5 |
| n-Butene | 42.0 |
| trans-2-Butene | 13.0 |
| cis-2-Butene | 9.5 |

Quantity = 4200.

Composition [% by weight] and quantity [kg/h] of stream 40:

| | |
|---|---|
| Propane | 0.1 |
| Propene | 0.1 |
| Propadiene | 0.05 |
| Propyne | 0.15 |
| n-Butane | 7.3 |
| i-Butane | 4.0 |
| n-Butene | 14.0 |
| i-Butene | 24.6 |
| trans-2-Butene | 4.5 |
| cis-2-Butene | 3.5 |
| 1,3-Butadiene | 40.0 |
| 1,2-Butadiene | 0.45 |
| Ethylacetylene | 0.2 |
| Vinylacetylene | 0.75 |
| i-Pentane | 0.1 |
| 3-Methyl-2-butene | 0.1 |
| 2-Methyl-2-butene | 0.1 |

Quantity = 15,000.

Quantity for stream 69 [kg/h]:
Quantity=1100.

Solvent required for the 3 extraction zones [kg/h] and composition thereof 8% by weight]:(HC=hydrocarbons)

| | | |
|---|---|---|
| (IExtr. zone) stream 42 = 165,000 with | NMP | 91.63 |
| | Water | 8.29 |
| | Total HC | 0.08 |
| Extr. zone (III) stream 46 = 35,000 with | NMP | 91.7 |
| | Water | 8.3 |
| | Total HC | 1 ppm by wt. |
| Extr. zone (II) stream 12 = 100,000 with | NMP | 91.63 |
| | Water | 8.29 |
| | Total HC | 0.08 |
| Stream 57 = 165,000 with | NMP | 91.7 |
| | Water | 8.3 |
| | Total HC | 1 ppm by wt. |

Temperature: generally 38° C.

In the following detailed description of the columns, the plate numbers are generally counted from the top of the column.

Operating conditions for column 100:

Number of theoretical plates = 4 + 50 (including back-wash zone)
HC back-flow to plate = 1
Solvent feed to plate = 5
HC feed to plate = 42
Added stream Zbc to plate = 42
Pressure at plate 1 = 4.0 bar
Temperature at plate 1 = 38.5° C.
HC back-flow quantity = 5000 kg/h Operating conditions for column 110:

Number of theoretical plates = 4 + 9 (including back-wash zone)
HC back-flow to plate = 1
Extract feed to plate = 5
Pressure at plate 1 = 1.526 bar
Temperature at plate 1 = 6.7° C.
HC back-flow quantity = 5000 kg/h
Energy required = 10,361 kW Operating conditions for column 120:

Number of theoretical plates = 25 + 23 + 7 (in 2 columns)
HC back-flow to plate = 1
Solvent feed to plate = 1
HC take-off at plate = 49 (to the extraction zone II)
HC feed to plate = 26
Pressure at plate 1 = 4.5 bar
Temperature at plate 1 = 41.5° C.
HC back-flow quantity = 2094 kg/h Operating conditions for column 130:

Number of theoretical plates = 4 + 30 (including back-wash zone)
HC back-flow to plate = 1
Solvent feed to plate = 5
Pressure at plate 1 = 5.0 bar
Temperature at plate 1 = 45.3° C.
HC back-flow quantity = 2120 kg/h Operating conditions for column 140:

Number of theoretical plates = 10
Extract feed to plate = 1
HC take-off at plate = 6 (to column 150)
Pressure at plate 1 = 1.52 bar
Temperature at plate 1 = 104.6° C.
Temperature at plate 10 = 146.1° C.
HC back-flow quantity = 2120 kg/h
Energy required = 6773 kW Operating conditions for column 150:

Number of theoretical plates = 2
Water feed to plate = 1
Extract feed to plate = 1
Pressure at plate 1 = 1.52 bar
Temperature at plate 1 = 108° C.

Operating conditions for column 160:

Number of theoretical plates = 46
HC back-flow to plate = 1
Extract feed to plate = 16
Pressure at plate 1 = 7 bar
Temperature at plate 1 = 46.6° C.
HC back-flow quantity = 6130 kg/h
Energy required = 761 kW Operating conditions for column 170:

Number of theoretical plates = 45
HC back-flow to plate = 1
Extract feed to plate = 23
Pressure at plate 1 = 4.2 bar
Temperature at plate 1 = 39.3° C.
HC back-flow quantity = 11197 kg/h
Energy required = 1671 kW The individual process steps are as follows:

The normally liquid $C_4$ hydrocarbon mixture (stream 40) is vaporized in the heat exchanger 240 and enters the extraction zone (I) as vapor, approximately in the middle of column 120. Solvent is passed via stream 42 countercurrently to the ascending gases. This results in two new streams: a gaseous product (stream 43) containing essentially the major quantity of propane, propene, propadiene, the butanes and the butenes, and an extract (stream 53) containing the hydrocarbons dissolved in the solvent, comprising 1,3-butadiene and the other hydrocarbons, including the $C_5$-hydrocarbons. The 1,3-butadiene content, an important specification quantity for the separation requirement of the exraction zone (I), is below 100 ppm by weight.

To lower the temperature profile in the column 120, 20% by weight of the gas stream 43 are condensed in the heat exchanger 230.

A side stream leaves the column 120 via stream 51 and is washed countercurrently with solvent (stream 46) in the extraction zone (II), which is column 130. To lower the temperature profile and, at the same time, to reduce the NMP loss, the column has a black-flow of liquid hydrocarbons (stream 50). The solvent quantity (stream 46) is adjusted so that the specifications relating to ethylacetylene and vinylacetylene for the later pure 1,3-butadiene are met. The decanter 320 incorporated in the top circulation serves for partial removal of water from the crude butadiene.

The extract from the extraction zone (I), which is stream 53, passes through a heat exchanger 255 and is then partially desorbed under pressure in the flash tank 410, resulting in two streams: a gaseous portion (stream 59) which is immediately recycled via stream 67 to the column 120, and a liquid portion (stream 60). The temperature of the stream 60, which is still under the elevated flash pressure in the flash tank 410, is raised by 5 C in another heat exchanger 260, before it is let down by reducing the pressure in the column 140.

The extract, stream 61, is almost completely desorbed from the $C_4$-hydrocarbons in column 140 by input of external energy. The resulting gas, stream 62, is cooled in the heat exchanger 265 to the abovementioned 45 C and divided in the flash tank 420 into a very small portion of liquid phase (stream 66) and the main part of gas phase (stream 64). The gas stream 64 is compressed in the compressor 500 and, after combining with the streams 59 and 66, returned as stream 67 to the lower part of the column 120.

A gas stream 68 is removed from column 140 approximately in the middle. Beside hydrocarbons, it contains water. This gas stream is washed countercurrently with condensate in the column 150, and the gaseous product (stream 70) is cooled in heat exchanger 270 and, after division into a gas phase and liquid phase (streams 72 and 73), discharged as product. The NMP content in stream 70 is about 160 ppm by weight, which signifies an NMP loss of 0.19 kg/h at this point.

The route taken by the almost completely desorbed solvent from the column 140 passes successively through the heat exchangers 255 (heating of the extract from column 120), 250 (reboiler for column 170), 240 (vaporization of the $C_4$-hydrocarbon mixture) and 235 (final solvent cooler to adjust the solvent temperature). It thus passes completely through the extraction zones (I) and (III) and the desorption zones (I) and (II).

The top product from column 120 (stream 45) and the added stream Zbc (stream 11) are fed into the lower third of the extraction zone (II), i.e. column 100. The gases are passed together with the gas stream resulting after heat exchange in the heat exchanger 215 and subsequent flash decompression in the flash tank 400 countercurrently to the solvent (streams 12 and 57). This results in a high-purity butane fraction (stream 13) with only 0.43% by weight of butenes. Like the top product from column 130, the gas stream 13 is also condensed (heat exchanger 200) and then partly freed of water in the decanter 300 before it is returned as liquid hydrocarbon back-flow (stream 16) to column 100 or is discharged as butane fraction (c), i.e. stream 17, as product.

The extract, which has already been heated by heat exchange, from the extraction zone (II), i.e. stream 20, is fed, after renewed indirect heat exchange in the heat exchanger 220 and after pressure reduction, to the desorption zone (III), i.e. column 110. The extract is very substantially freed of the $C_4$-hydrocarbons therein by input of external heat. The butene fraction (b) thus resulting, stream 23, is likewise of high purity and contains only 1.85% by weight of butanes. After condensation in the heat exchanger 225 and partial removal of water in the decanter 225, the butene fraction is partly fed in liquid form as back-flow into column 110 (stream 26) and partly discharged as product (stream 27).

The heat exchanger 225 requires a refrigerant because of the low condensation temperature of the butene fraction. It is not possible to increase the pressure level in column 110: on the one hand, the bottom temperature of column 110 would exceed the limit of 150° C., which would be equivalent to impermissible thermal stress on the solvent and, on the other hand, the desorption of the hydrocarbons would be impeded, which could be compensated only by additional input of external energy.

The solvent desorbed in the column 110 passes successively through the heat exchangers 220 (extract preheating), 215 (raising the temperature of the extract for the purpose of the pressure flash), 210 (vaporizer of the added stream 10) and 205 (final cooler for adjusting the solvent temperature). Because of the variety of tasks, certain temperature levels are preset, for which reason the hydrocarbon content of stream 28 cannot be indefinitely high. In the exemplary case, the concentration is 800 ppm by weight. This means that it also passes completely through the absorption and desorption zones (III).

There only remains the area with the distillation columns 160 and 170 for final adjustment of the specifications of the 1,3-butadiene fraction (a). The crude butadiene (stream 80) is fed into the upper third of column 160. The gaseous top product (stream 81) is condensed and, after partial removal of water in a decanter 330, both recycled as liquid hydrocarbon back-flow (stream 84) to column 160, and discharged as product (stream 83). It should be noted that stream 81 must not exceed a certain propyne concentration for safety reasons. This limiting concentration is pressure-dependent. Its value is 50% by volume at a top pressure of 7 bar.

The almost anhydrous bottom discharge from the column 160 is fed into column 170 approximately in the middle. The mixture is fractionated therein to a high-purity 1,3-butadiene fraction (stream 89) and a bottom product (stream 91), with stream 91 representing a mixture mainly of the hydrocarbons cis-2-butene, 1,3-butadiene, 1,2-butadiene and $C_5$-hydrocarbons. The 1,3-butadiene yield can be influenced by the preset 1,3-butadiene concentration. This is 25% by weight in the present example. The product specification of fraction (a), i.e. the pure butadiene, is as follows:

1,3-Butadiene = 99.6% by weight
Total butenes = 0.4% by weight
Propyne = 10 ppm by weight
1,2-Butadiene = 50 ppm by weight
Total $C_4$-acetylenes < 5 ppm by weight
Total $C_5$-HC < 5 ppm by weight In conclusion, the amounts of energy [kW] exchanged for condensers and heat exchangers are listed below:

| Heat exchanger | 200:785 |
| Heat exchanger | 205:8991 |
| Heat exchanger | 210:482 |
| Heat exchanger | 215:3127 |
| Heat exchanger | 220:4000 |
| Heat exchanger | 225:1679 |
| Heat exchanger | 230:230 |
| Heat exchanger | 235:2945 |
| Heat exchanger | 240:1772 |
| Heat exchanger | 245:857 |
| Heat exchanger | 250:1671 |
| Heat exchanger | 255:7264 |
| Heat exchanger | 260:744 |
| Heat exchanger | 265:1729 |
| Heat exchanger | 270:572 |
| Heat exchanger | 275:693 |
| Heat exchanger | 280:1757 |

We claim:

1. A process for separating a $C_4$-hydrocarbon mixture comprising 1,3-butadiene, butenes, butanes and other $C_4$-hydrocarbons, into at least 4 fractions;

a) the fraction A (Fa) (Fa1) (Fa2) (Fa3) comprising 1,3-butadiene, b) the fraction B (Fb) comprising butenes, c) the fraction C (Fc) comprising butanes and d) one or more fractions D (Fd) (FdR) comprising 1,3-butadiene and the other $C_4$-hydrocarbons, comprising extractive distillation of said $C_4$-hydrocarbon mixture with N-methyl-2-pyrrolidinone or an aqueous solution of N-methyl-2-pyrrolidinone (NMP), wherein:

1. the $C_4$-hydrocarbon mixture in gaseous form is first brought into contact with NMP in an extraction zone (I) to form an extraction solution (Ead), the ratio of NMP to $C_4$-hydrocarbon mixture being from 5:1 to 20:1, the 1,3-butadiene and the other $C_4$-hydrocarbon is being essentially completely absorbed by the NMP but the butenes and butanes remaining essentially in the gas phase to form a gas stream (Gbc);

2. the unabsorbed butenes and butanes (Gbc) and the extraction solution (Ead) formed in step 1 are removed from the extraction zone (I);

3. the extraction solution (Ead) is transferred to a desorption zone (I) at a lower pressure and/or higher temperature than the extraction zone (I) and 1,3-butadiene is desorbed from the extraction solution (Ead) to form the fraction A (Fa), the main part of the other $C_4$-hydrocarbons remain in the liquid phase to form an extraction solution (Ed);

4. the extraction solution (Ed) formed in step 3 and the desorbed 1,3-butadiene (Fa) are removed separately from the desorption zone (I) and, if required, a part of the fraction A is returned to the extraction zone (I);

5. the extraction solution (Ed) is transferred to a second desorption zone (II) at a lower pressure and/or higher temperature than the desorption zone (I) and having a pressure and/or temperature gradient, and the other $C_4$-hydrocarbon is and the 1,3-butadiene still remaining therein are fractionally desorbed from the extraction solution (Ed) to form at least two separate fractions D (Fd) (FdR), with the content of the other $C_4$-hydrocarbons being at least 10 times higher in at least one of the fractions (Fd) than in the extraction solution (Ed), based on the content of all $C_4$-hydrocarbons, and the content of the other $C_4$-hydrocarbons being correspondingly lower in at least one of the fractions (FdR) than in the fractions D, based on the content of all $C_4$-hydrocarbons, and the extraction solution (Ed) further forming NMP, 6. the NMP, formed in the desorption zone (II) and essentially free of $C_4$-hydrocarbons, and the fractions (Fd) and (FdR) are removed separately from the desorption zone (II), and one or more fractions (FdR) are returned to the desorption zone (I), 7. the gas stream (Gbc) is first brought into contact with NMP in an extraction zone (II) to form an extraction solution (Eb), the butenes being essentially completely absorbed by the NMP but the butanes remaining essentially in the gas phase;

8. the unabsorbed butanes (fraction C (Fc)) and the extraction solution (Eb) formed in step 7 are removed from the extraction zone (II);

9. the extraction solution (Eb) is transferred to a desorption zone (III) at a lower pressure and/or higher temperature than the extraction zone (II) and the butenes are desorbed from the extraction solution (Eb) to form NMP essentially free of $C_4$-hydrocarbons;

10. the NMP, formed in step 9 and essentially free of $C_4$-hydrocarbon is, and the desorbed butenes (fraction B (Fb)) are removed from the desorption zone (III);

11. the NMP formed in step 9 is recycled to the extraction zones (I) and (II), 12. a part of the 1,3-butadienie fraction A (Fa1) which is removed from the desorption zone (I) is returned to the extraction zone (I), and the other part (Fa2) is again brought into contact, in an extraction zone (III), with NMP which was recovered according to step 6, the ratio of NMP to the crude butadiene fraction (Fa2) being from 1:3 to 1:7 and a part of the fraction (Fa2) and the predominant part of other $C_4$-hydrocarbons still contained as impurity in the fraction (Fa2) being absorbed by the NMP to form an extraction solution (Eax); and 13. the unabsorbed part of the fraction (Fa2) ((Fa3)) is removed separately from the extraction zone (III), and the extraction solution (Eax) is returned to the extraction zone (I).

2. A process as claimed in claim 1, wherein the NMP and the $C_4$-hydrocarbon mixture are fed into the extraction zone (I) in a ratio by weight of from 5:1 to 20:1.

3. A process as claimed in claim 1, wherein the $C_4$-hydrocarbon mixture contains from 10 to 80% by weight of 1,3-butadiene;

from 10 to 60% by weight of butenes;

from 5 to 40% by weight of butanes; and from 0.1 to 5% by weight of other $C_4$-hydrocarbons.

4. A process as claimed in Claim 1, wherein the extraction zone (I) is in the form of 2 columns connected to one another.

5. A process as claimed in claim 1, wherein the extraction zones (I), (II) and (III) are in the form of columns and the fractions and $C_4$-hydrocarbon mixture are passed countercurrently to the NMP through said columns.

6. A process as claimed in claim 1, wherein the desorption described in steps 3 and 5 of claim 1 is effected by increasing the temperature in the desorption zone (I) relative to that in the extraction zone (I) and increasing the temperature in the desorption zone (II) relative to that in the desorption zone (I) by supplying the heat of the NMP, which has been removed according to step 11 of claim 1 from the desorption zone (II), to the desorption zone (I) by indirect heat exchange in a heat exchange zone.

7. A process as claimed in claim 1, wherein another hydrocarbon stream (added stream Zbc), the latter essentially consisting of a mixture of butanes and butenes, is added to the gas stream formed in step 1.

8. A process as claimed in claim 1, wherein the temperature is increased in the desorption zones (II) and (III) for the purpose of complete desorption of the NMP from hydrocarbons by indirect heat exchange with steam.

9. A process as claimed in claim 1, wherein the back gas required for separating the fractions (b) and (c) is obtained in the extraction zone (II) by partial desorption of the extraction solution (Eb), the required increase in temperature originating, by indirect heat exchange, from the NMP freed of $C_4$-hydrocarbons in the desorption zone (III).

* * * * *